(12) United States Patent
Bonrath et al.

(10) Patent No.: US 9,108,925 B2
(45) Date of Patent: Aug. 18, 2015

(54) PROCESS FOR THE MANUFACTURE OF A PRECURSOR OF VITAMIN B1

(75) Inventors: Werner Bonrath, Freiburg (DE); Jocelyn Fischesser, Wittenheim (FR); Lisa Giraudi, Huningue (FR); Reinhard Karge, Staufen (DE)

(73) Assignee: DSM IP ASSETS B.V., Heerlen (NL)

( * ) Notice: Subject to any disclaimer, the term of this patent is extended or adjusted under 35 U.S.C. 154(b) by 1217 days.

(21) Appl. No.: 11/795,957

(22) PCT Filed: Jan. 24, 2006

(86) PCT No.: PCT/EP2006/000600
§ 371 (c)(1), (2), (4) Date: Jul. 25, 2007

(87) PCT Pub. No.: WO2006/079504
PCT Pub. Date: Aug. 3, 2006

(65) Prior Publication Data
US 2008/0242863 A1    Oct. 2, 2008

(30) Foreign Application Priority Data
Jan. 28, 2005    (EP) .................................... 05001859

(51) Int. Cl.
*C07D 239/42* (2006.01)
*C07D 239/50* (2006.01)
*C07D 417/06* (2006.01)

(52) U.S. Cl.
CPC ............ *C07D 239/42* (2013.01); *C07D 417/06* (2013.01)

(58) Field of Classification Search
CPC ............................ C07D 239/50; C07D 239/42
USPC ......................................................... 544/326
See application file for complete search history.

(56) References Cited

U.S. PATENT DOCUMENTS 2,775,592 A * 12/1956 Takamizawa ................. 544/256

FOREIGN PATENT DOCUMENTS

DE    3511273 A1 * 10/1986
EP    1138675 A2 * 10/2001

OTHER PUBLICATIONS

Machine Translation of DE 3511273, published Oct. 9, 1986.*

* cited by examiner

*Primary Examiner* — Venkataraman Balasubramanian
(74) *Attorney, Agent, or Firm* — Nixon & Vanderhye P.C.

(57) ABSTRACT

The present invention relates to a novel process for the manufacture of Grewe-diamine comprising the following step: hydrolyzing a compound of formula (II),

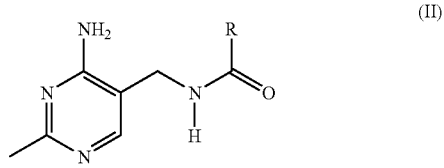

wherein R is hydrogen or straight- or branched chain C1-4 alkyl, with an aqueous alkali or alkaline-earth metal hydroxide solution, characterized in that the hydrolysis is carried out in the presence of an organic solvent.

27 Claims, 3 Drawing Sheets

PROCESS FOR THE MANUFACTURE OF A PRECURSOR OF VITAMIN B1

Figure 1:
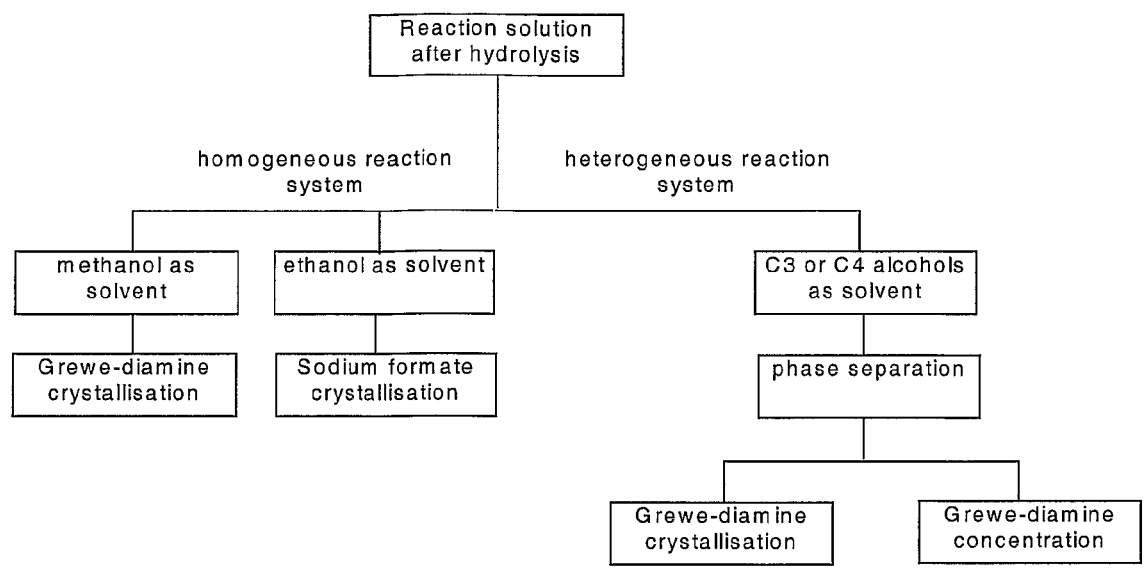

This application is the US national phase of international application PCT/EP2006/000600 filed 24 Jan. 2006 which designated the U.S. and claims benefit of EP 05001859.7, dated 28 Jan. 2005, the entire content of which is hereby incorporated by reference.

The present invention relates to a novel process for the manufacture of Grewe-diamine (GDA; 5-aminomethyl-2-methyl-pyrimidine-4-yl-amine) of formula I

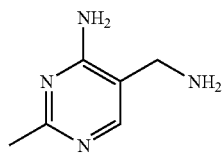

by hydrolysis of a N-(4-amino-2-methyl-pyrimidine-5-yl-methyl)-alkanamide with an aqueous alkali or alkaline earth metal hydroxide solution. More precisely, the present invention relates to the hydrolysis of such N-substituted alkanamide wherein the hydrolysis is carried out in the presence of an organic solvent, preferably in the presence of an organic solvent with a dielectric constant from 7 to 35, more preferably in the presence of an organic solvent which is essentially not soluble in water under the reaction conditions.

GDA is an important precursor for the synthesis of vitamin $B_1$, see e.g. G. Moine and H-P. Hohmann in Ullmann's Encyclopedia of Industrial Chemistry, VCH, Vol. A 27, 1996, 515-517 and the references cited therein.

To perform the processes described in the prior art (EP-A 1 138 675, DE-A 35 11 373), i.e. the hydrolysis of N-acetyl GDA or N-formyl GDA, drastic reaction conditions are necessary. The process described in DE-A 35 11 373 has the disadvantage that the overall yield is low and that the product has to be further purified by sublimation.

Therefore, there existed a need for a process for the manufacture of GDA where the product is obtained in high yield and high purity.

This need is fulfilled by a process for the manufacture of Grewe-diamine comprising the following step (step a): hydrolyzing a compound of formula II,

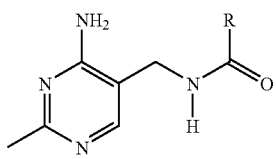

wherein R is hydrogen or straight- or branched-chain $C_{1-4}$ alkyl, with an aqueous alkali or alkaline earth metal hydroxide solution in the presence of an organic solvent.

Concerning substituent R: Substituent R is hydrogen, methyl, ethyl, propyl or butyl. Preferably R is hydrogen, methyl, ethyl, n-propyl or n-butyl, more preferably R is hydrogen or methyl; most preferably R is hydrogen.

The manufacture of the compound of formula II is known to the person skilled in the art and may be, e.g., performed as described in any of JP 58-065 279 (publication number; application number: 56-162 106), EP-A 0 172 515, EP-A 0 001 760, U.S. Pat. No. 4,226,799 and DE-A 35 11 273.

Concerning the organic solvent: Examples of suitable organic solvents are such organic solvents that have a dielectric constant ($\in$r) in the range from 7 to 35 (see C. Reichardt, Solvents and Solvent Effects in Organic Chemistry, VCH, 1988, p. 408-410). Examples of preferred solvents are aliphatic alcohols, especially aliphatic $C_{1-4}$-alcohols, ethers and mixtures thereof. Examples of more preferred solvents are those which are essentially not soluble in water under the reaction conditions.

"Essentially not soluble in water under the reaction conditions" means that a biphasic liquid system is formed. A biphasic liquid system is, e.g., formed under the reaction conditions with aliphatic $C_{3-4}$-alcohols, ethers and mixtures thereof.

Examples of aliphatic $C_{1-4}$-alcohols are methanol, ethanol, propan-1-ol, propan-2-ol, butan-1-ol, butan-2-ol, 2-methyl-propan-2-ol, and 2-methyl-propan-1-ol.

The most preferred aliphatic $C_{3-4}$-alcohols are selected from the group consisting of propan-1-ol, propan-2-ol, butan-1-ol, butan-2-ol, and 2-methyl-propan-2-ol, more preferably selected from the group consisting of propan-2-ol, butan-1-ol, and butan-2-ol. These are also the most preferred organic solvents used in the process according to the present invention.

Preferred ethers are ethers, in which GDA is soluble. The most preferred ethers are tetrahydrofuran, and 1,2-dimethoxyethane.

Concerning the alkali and alkaline earth metal hydroxide: Examples are sodium, potassium, caesium, calcium and magnesium hydroxide with sodium hydroxide being preferred.

Concerning the alkali and alkaline earth metal hydroxide solution: Preferably the solution has a concentration in the range of from 5 to 30 weight-%, more preferably in the range of from 15 to 28 weight-%.

Reaction Conditions:

Conveniently the hydrolysis (step a) is carried out at a temperature in the range of from 20 to 110° C., preferably at a temperature in the range of from 30° C. to 90° C., more preferably at a temperature in the range of from 40° C. to 85° C.

Conveniently the reaction time is in the range of from 30 to 240 minutes, preferably in the range of from 30 to 120 minutes.

Conveniently the reaction is carried out at normal pressure and may be carried out under air atmosphere.

In specific embodiments of the invention the process comprises further steps. These steps depend on the organic solvent used (in step a).

If the hydrolysis (step a) is, e.g., carried out in the presence of an organic solvent which is essentially not soluble in water under the reaction conditions the process may further comprise additional steps b1), c1), d1) and d2) (see below).

If the hydrolysis (step a) is carried out in the presence of methanol the process may further comprise additional step b2) (see below).

If the hydrolysis (step a) is carried out in the presence of ethanol the process may further comprise additional steps b3), c3) and d3) (see below).

If the hydrolysis (step a) is carried out in the presence of an organic solvent which is essentially not soluble in water under the reaction conditions the process of the present invention preferably comprises the following additional step(s)

b1) phase separating the reaction mixture after the end of the reaction in an aqueous and in an organic phase;

c1) optionally extracting the aqueous phase with the solvent being essentially not soluble in water and combining the organic phases.

Step b1):

The aqueous phase, i.e. the aqueous alkali or alkaline earth metal hydroxide solution, and the solvent being essentially not soluble in water form a biphasic liquid system. After the end of the reaction, i.e., when the compound of the formula II has been hydrolysed to GDA, the two phases are separated from each other. The aqueous phase contains the alkali or alkaline earth metal formate formed during the reaction and the organic phase contains the solvent and the product.

Preferably the phase separation is performed at a temperature in the range of from 40° C. to 80° C., more preferably at a temperature in the range of from 50° C. to 70° C.

In a preferred embodiment of the invention steps a), b1) and c1) are performed subsequently in the order given (which is the best mode of the invention).

According to other specific embodiments of the process of the present invention the isolation of the product GDA may be effected by either of two alternatives d1) and d2) for the workup.

Alternative 1 (Step d1)):

After the steps a), b1) and c1) have been performed the solvent being essentially not soluble in water is evaporated from the organic phase. This evaporation is preferably carried out at a temperature of from 40° C. to 80° C. and/or at a pressure of from 5 to 30 mbar.

Alternative 2 (Step d2)):

After the steps a), b1) and c1) have been performed the GDA is crystallised from the separated organic phase. This may be achieved by cooling down the organic phase, preferably to a temperature of from 20 to −10° C., more preferably to a temperature of from 5 to 0° C. From the mother liquor additional GDA can be crystallised. The GDA crystals are then separated from the liquid.

If the hydrolysis (step a) is carried out in the presence of methanol the process preferably further comprises step b2):

b2) crystallising the Grewe-diamine from the reaction solution.

This may be achieved by cooling down the reaction solution, preferably to a temperature in the range of from 20 to −10° C., more preferably to a temperature in the range of from 5 to 0° C. From the mother liquor additional GDA can be crystallised. The GDA crystals are then separated from the liquid.

If the hydrolysis (step a) is carried out in the presence of ethanol the process preferably further comprises steps b3), c3) and d3):

b3) crystallising the by-product alkali or alkaline earth formate from the reaction solution, c3) separating the crystallised alkali or alkaline earth formate from the reaction solution, and d3) evaporating water and ethanol from the remaining reaction solution.

Step b3) may be achieved by cooling down the reaction solution, preferably to a temperature in the range of from 20 to −10° C., more preferably to a temperature in the range of from 5 to 0° C. From the mother liquor additional alkali or alkaline earth metal formate can be crystallised.

A further advantage of the process of the present invention, besides the high yield (preferably ≥98%) and the high purity of the product (preferably ≥97%), is that the GDA obtained is essentially free from aniline, 2-chloroaniline and/or from any alkali or alkaline earth metal formate. In a preferred embodiment of the invention the content of 2-chloroaniline is below <250 ppm and/or the content of any alkali or alkaline earth metal formate formed during the hydrolysis is below 2%.

The thus obtained GDA may, e.g., be further reacted with carbon disulfide and 3-chloro-5-acetoxypentan-2-one or another chloroketone derivate such as 3-chloro-5-hydroxypentan-2-one, 3-mercapto-5-hydroxypentan-2-one or 3-mercapto-5-acetoxypentan-2-one to form the compound of formula III

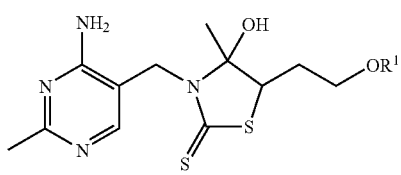

with $R^1$ being $C_{1-4}$-alkanoyl, preferably acetyl (see e.g. G. Moine and H-P. Hohmann in Ullmann's Encyclopedia of Industrial Chemistry, VCH, Vol. A 27, 1996, 515-517 and the references cited therein).

Therefore, such a process for the manufacture of a compound of the formula III is also a part of the present invention.

The compound of formula III may then further be reacted with an acid to form the compound of formula IV

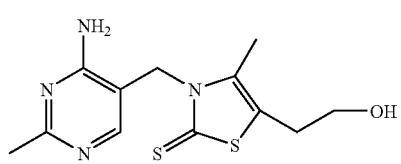

(see e.g. G. Moine and H-P. Hohmann in Ullmann's Encyclopedia of Industrial Chemistry, VCH, Vol. A 27, 1996, 515-517 and the references cited therein).

Therefore, such a process for the manufacture of a compound of formula IV is also a part of the present invention.

The compound of the formula IV may then further be oxidized, preferably with $H_2O_2$, to vitamin $B_1$ of formula V

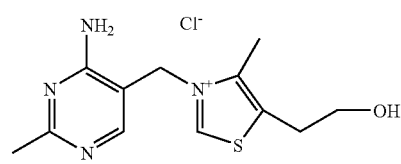

(see e.g. G. Moine and H-P. Hohmann in Ullmann's Encyclopedia of Industrial Chemistry, VCH, Vol. A 27, 1996, 515-517 and the references cited therein).

Therefore, the present invention comprises a process for the manufacture of vitamin $B_1$ wherein a compound of formula II

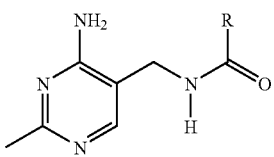

with R being hydrogen or straight- or branched chain $C_{1-4}$ alkyl is hydrolysed to Grewe-diamine according to the process of the present invention described above in detail, the thus obtained Grewe-diamin is further reacted to a compound of formula IV,

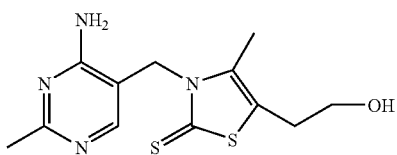

preferably as described above in more detail, and the thus obtained compound of formula IV is further oxidized, preferably with $H_2O_2$, to yield vitamin B1.

Finally the present invention comprises the use of GDA obtained according to the process of the present invention as described above as intermediate in a process for the manufacture of vitamin B1.

FIGS. 1, 2 AND 3

FIG. 1: Overview over the isolation methods.

Figure 2:
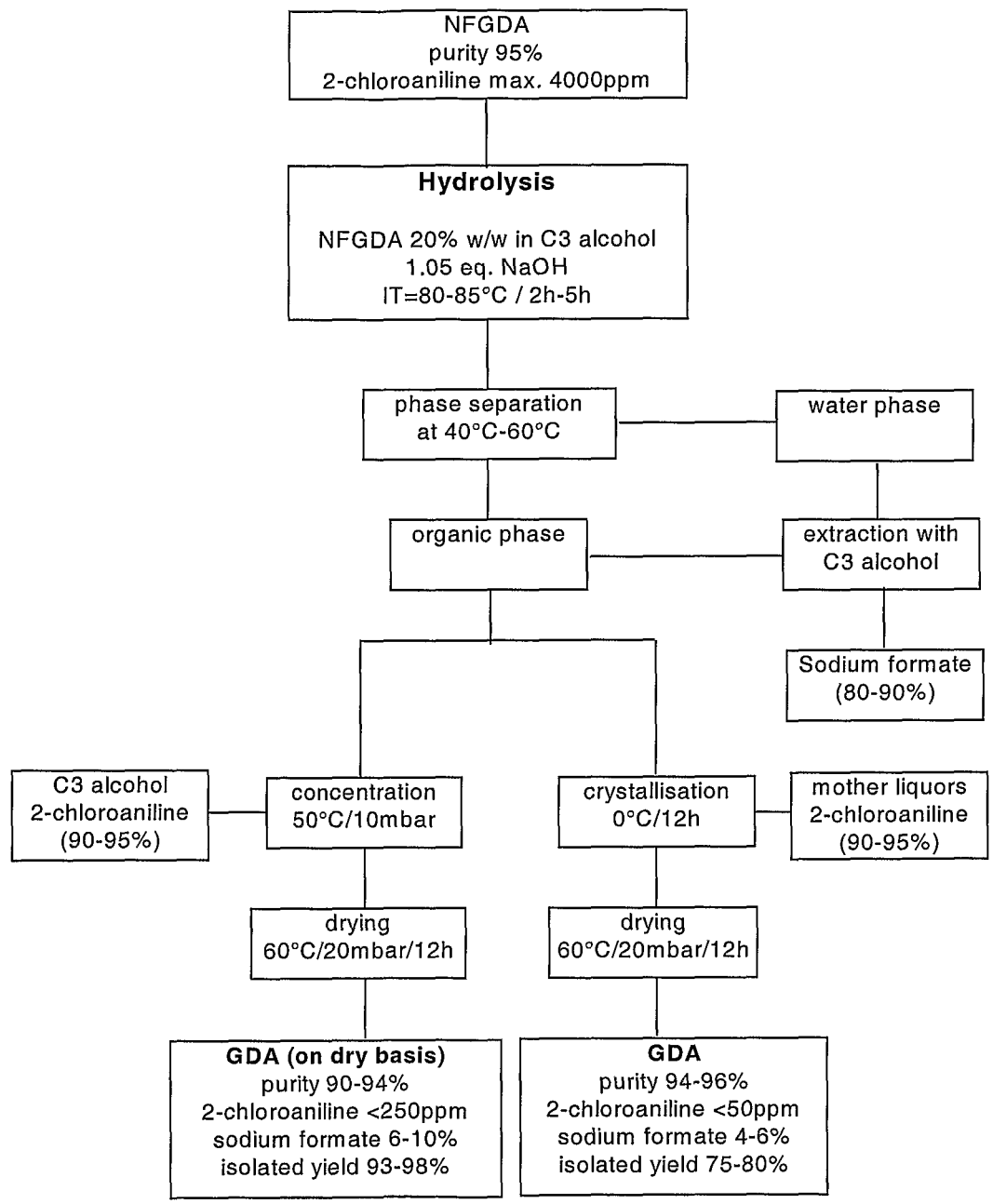

FIG. 2: NFGDA (=N-formyl Grewe-diamine) hydrolysis and waste separation in $C_3$-alcohols.

Figure 3:
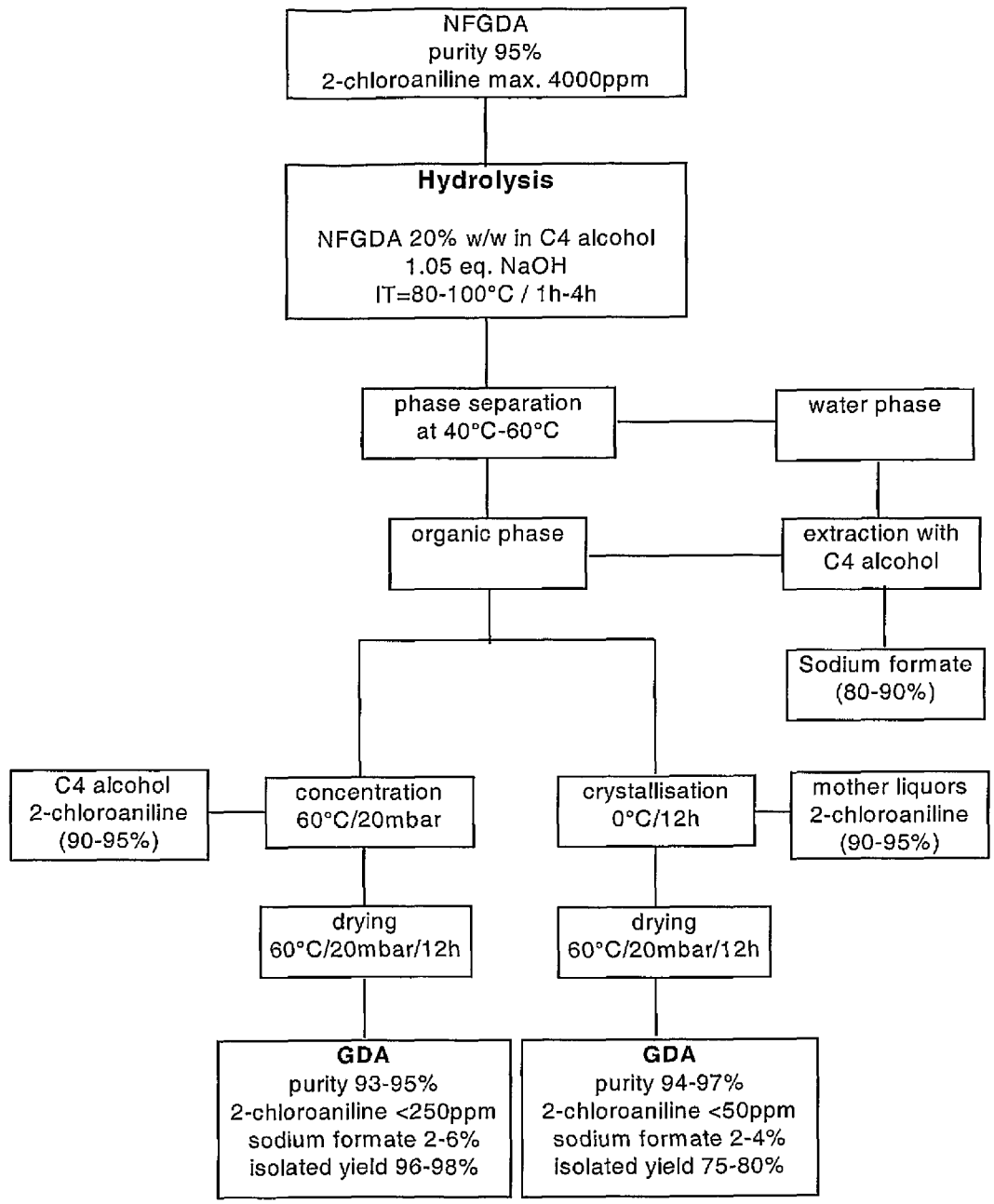

FIG. 3: NFGDA (=N-formyl Grewe-diamine) hydrolysis and waste separation in $C_4$-alcohols.

In the figures the following abbreviations are used: "NFGDA"=N-Formyl GDA, "IT"=internal temperature, "w/w"=weight/weight, "eq."=mol equivalents, "h"=hour(s).

FIG. 1 gives a short overview over the processes wherein methanol or ethanol are used as a solvent for the hydrolysis of a compound of the formula II (left side) and the processes wherein aliphatic $C_3$- or $C_4$-alcohols are used as a solvent for the hydrolysis of a compound of the formula II (right side).

When methanol or ethanol are used as a solvent for the hydrolysis of a compound of the formula II the reaction solution is a homogeneous reaction system, whereas when aliphatic $C_3$- or $C_4$-alcohols are used as a solvent for the same purpose the reaction solution is a heterogeneous reaction system.

If methanol is used as the solvent, the GDA may be obtained by crystallisation out of the reaction solution.

If ethanol is used as the solvent, the by-product sodium formate is separated from the product GDA by crystallisation. The GDA itself is then obtained by concentration of the solution after separation of the crystalline sodium formate (see table 2 below).

When aliphatic $C_3$- or $C_4$-alcohols or mixtures thereof are used as the solvent the water and the organic phase are separated at the end of the reaction and the GDA is either obtained by concentration of the organic phase (see alternative 1 above) or by crystallisation of the GDA out of the organic phase (see alternative 2 above).

FIG. 2 shows a scheme of an example of the work-up and isolation of the hydrolysed GDA according to the present invention when the hydrolysis is performed in an aliphatic $C_3$-alcohol or mixtures thereof. As starting material NFGDA with a purity of 95% and a content of 2-chloroaniline of a maximum of 4000 ppm is used. The hydrolysis is carried out by reacting a $C_3$-alcohol solution containing 20 weight-% NFGDA (based on the total amount of the reaction solution) with an aqueous NaOH solution containing 1.05 mol equivalents of NaOH (based on the molar amount of NFGDA) at a temperature of from 80 to 85° C. for 2 to 5 hours. Afterwards the organic and the aqueous phase are separated from each other at a temperature of from 40 to 60° C.

The water phase is extracted with the $C_3$-alcohol and then evaporated to regain the sodium formate in a yield of 80 to 90% based on the amount of the sodium formate (=amount of NFGDA used) formed during the hydrolysis (see right side of the figure).

For the work-up of the organic phase there are two alternatives:

According to alternative 1 (left side) the organic phase is concentrated, i.e. the solvent is evaporated, at a temperature of 50° C. and at a pressure of 10 mbar. In the thus separated $C_3$-alcohol 90-95% of the 2-chloroaniline contained in the starting material are found. The thus isolated GDA is further dried at a temperature of 60° C. and at a pressure of 20 mbar for 12 hours. The thus obtained GDA has a purity of 90-94%, a content of 2-chloroaniline below 250 ppm, it contains 6-10% of sodium formate and the isolated yield of GDA (based on the amount of NFGDA used) is 93-98%.

According to alternative 2 (middle) the organic phase is cooled to a temperature of 0° C. for 12 hours whereby the GDA crystallises. The separated crystals are then dried at a temperature of 60° C. and at a pressure of 20 mbar for 12 hours. The thus obtained GDA has a purity of 94-96%, a content of 2-chloroaniline below 50 ppm, it contains 4-6% of sodium formate and the isolated yield of GDA (based on the amount of NFGDA used) is 75-80%.

FIG. 3 shows a scheme of an example of the work-up and isolation of the hydrolysed GDA according to the present invention when the hydrolysis is performed in an aliphatic $C_4$-alcohol or mixtures thereof. As starting material NFGDA with a purity of 95% and a maximum content of 2-chloroaniline of 4000 ppm is used. The hydrolysis is carried out by reacting a $C_4$-alcohol solution containing 20 weight-% NFGDA (based on the total amount of the reaction solution) with an aqueous NaOH solution containing 1.05 mol equivalents of NaOH (based on the molar amount of NFGDA) at a temperature of from 80 to 100° C. for 1 to 4 hours. Afterwards the organic and the aqueous phase are separated from each other at a temperature of from 40 to 60° C.

The water phase is extracted with the $C_4$-alcohol and then evaporated to regain the sodium formate in a yield of 80 to 90% based on the amount of the sodium formate (=amount of NFGDA used) formed during the hydrolysis (see right side of the figure).

For the work-up of the organic phase there are two alternatives:

According to alternative 1 (left side) the organic phase is concentrated, i.e. the solvent is evaporated, at a temperature of 60° C. and at a pressure of 20 mbar. In the thus separated $C_4$-alcohol 90-95% of the 2-chloroaniline contained in the starting material are found. The thus isolated GDA is further dried at a temperature of 60° C. and at a pressure of 20 mbar for 12 hours. The thus obtained GDA has a purity of 93-95%, a content of 2-chloroaniline below 250 ppm, it contains 2-6% of sodium formate and the isolated yield of GDA (based on the amount of NFGDA used) is 96-98%.

According to alternative 2 (middle) the organic phase is cooled to a temperature of 0° C. for 12 hours whereby the GDA crystallises. The separated crystals are then dried at a temperature of 60° C. and at a pressure of 20 mbar for 12 hours. The thus obtained GDA has a purity of 94-97%, a content of 2-chloroaniline below 50 ppm, it contains 2-4% of sodium formate and the isolated yield of GDA (based on the amount of NFGDA used) is 75-80%.

The present invention is further illustrated by the following examples.

EXAMPLES

The hydrolysis conditions, the isolation method of GDA as well as the isolation method of sodium formate of the examples 1 to 33 are described shortly in the following tables 1 to 9. For the examples 3-8, 10, 11, 13, 15 and 17-33 only this short description is given.

The following abbreviations are used:
"NFGDA" means N-formyl Grewe-diamine (compound II with R=hydrogen), "ML" means mother liquor, "rpm" means rounds per minute; "GC" means gas chromatography, "HPLC" means high performance/pressure liquid chromatography, "int." means internal, "ext." means external, "overnight" means 12 hours.

TABLE 1

Examples 1 to 4

| | Example | | | |
|---|---|---|---|---|
| | 1 | 2 | 3 | 4 |
| Hydrolysis conditions | | | | |
| NFGDA [mmol] | 53.5 | 107 | 200 | 300 |
| NaOH [mol equivalents] | 1.05 | 1.05 | 1.05 | 1.05 |
| Solvent | methanol | ethanol | ethanol | propan-1-ol |
| Amount of solvent [mol equivalents] | 9.7 | 9.7 | 7.0 | 9.7 |
| Concentration [% NFGDA] | 26.5 | 22.0 | 25.0 | 18.8 |
| Temperature [° C.] | 76 | 80 | 80 | 80 |
| Time [hour(s)] | 4.5 | 4.0 | 4.0 | 5.0 |
| Isolation method of GDA | Crystallisation & concentration of ML | Concentration of solution | Concentration of solution | Concentration of solution |
| Isolation method of sodium formate | | Crystallisation | Crystallisation | Phase separation |
| Crystallisation | | | | |
| Temperature [° C.] | 1 | | | |
| Time [hour(s)] | 12 | | | |
| Yield Crystallisation [%] | 35.9 | | | |
| Yield Mother Liquor (ML) [%] | 60.0 | | | |
| Total Yield [%] | 95.9 | | | |

TABLE 2

Examples 5 to 8

| | Example | | | |
|---|---|---|---|---|
| | 5 | 6 | 7 | 8 |
| Hydrolysis conditions | | | | |
| NFGDA [mmol] | 300 | 1000 | 300 | 300 |
| NaOH [mol equivalents] | 1.05 | 1.05 | 1.05 | 1.05 |
| Solvent | propan-1-ol | propan-2-ol | propan-2-ol | propan-2-ol |
| Amount of solvent [mol equivalents] | 4.0 | 10.6 | 9.7 | 9.7 |
| Concentration [% NFGDA] | 30.0 | 16.4 | 18.8 | 18.8 |
| Temperature [° C.] | 94 | 82 | 80 | 80 |
| Time [hour(s)] | 4.5 | 4.0 | 4.5 | 5.0 |
| Isolation method of GDA | second extraction of H$_2$O | second extraction of H$_2$O | Concentration of solution | Crystallisation & concentration of ML |

TABLE 2-continued

Examples 5 to 8

| | Example | | | |
|---|---|---|---|---|
| | 5 | 6 | 7 | 8 |
| Isolation method of sodium formate Crystallisation | Crystallisation & concentration of ML<br>Phase separation | Concentration of solution<br>Phase separation | Phase separation | Phase separation |
| Temperature [° C.] | 1 | | | 20 |
| Time [hour(s)] | 12 | | | 12 |
| Yield Crystallisation [%] | 73.8 | | | 42.5 |
| Yield Mother Liquor (ML) [%] | 17.9 | | | 51.5 |
| Total Yield [%] | 91.7 | | | 94.0 |

TABLE 3

Examples 9 to 12

| | Example | | | |
|---|---|---|---|---|
| | 9 | 10 | 11 | 12 |
| Hydrolysis conditions | | | | |
| NFGDA [mmol] | 300 | 200 | 300 | 300 |
| NaOH [mol equivalents] | 1.05 | 1.05 | 1.05 | 1.05 |
| Solvent | propan-2-ol | propan-2-ol | propan-2-ol | propan-2-ol |
| Amount of solvent [mol equivalents] | 9.7 | 9.7 | 4.9 | 4.0 |
| Concentration [% NFGDA] | 18.8 | 18.9 | 27.6 | 30.0 |
| Temperature [° C.] | 83 | 80 | 80 | 84 |
| Time [hours] | 5.5 | 4.5 | 5.0 | 4.0 |
| Isolation method of GDA | second extraction of H$_2$O<br>Concentration of solution | second extraction of H$_2$O<br>Concentration of solution | Crystallisation & concentration of ML | second extraction of H$_2$O<br>Crystallisation & concentration of ML |
| Isolation method of sodium formate Crystallisation | Phase separation | Phase separation | Phase separation | |
| Temperature [° C.] | | | 1 | 1 |
| Time [hours] | | | 12 | 12 |
| Yield Crystallisation [%] | | | 75.4 | 76.6 |
| Yield Mother Liquor (ML) [%] | | | 13.4 | 16.8 |
| Total Yield [%] | | | 88.8 | 93.4 |

TABLE 4

Examples 13 to 16

| | Example | | | |
|---|---|---|---|---|
| | 13 | 14 | 15 | 16 |
| Hydrolysis conditions | | | | |
| NFGDA [mmol] | 300 | 200 | 300 | 1000 |
| NaOH [mol equivalents] | 1.05 | 1.05 | 1.05 | 1.05 |
| Solvent | propan-2-ol | butan-1-ol | butan-1-ol | butan-1-ol |
| Amonunt of sovlent [mol equivalents] | 3.0 | 10.0 | 10.0 | 7.8 |

TABLE 4-continued

Examples 13 to 16

| | Example | | | |
|---|---|---|---|---|
| | 13 | 14 | 15 | 16 |
| Concentration [% NFGDA] | 33.5 | 16.1 | 16.1 | 16.1 |
| Temperature [° C.] | 85 | 100 | 100 | 100 |
| Time [hour(s)] | 3.5 | 1.5 | 3.0 | 4.0 |
| Isolation method of GDA | second extraction of $H_2O$ Crystallisation & concentration of ML | Crystallisation & concentration of ML | second extraction of $H_2O$ Concentration | second. extraction of $H_2O$ Concentration |
| Isolation method of sodium formate Crystallisation | | Phase separation | Phase separation | |
| Temperature [° C.] | 1 | 1 | | |
| Time [h] | 12 | 12 | | |
| Yield Crystallisation [%] | 77.4 | 82.7 | | |
| Yield Mother Liquor (ML) [%] | 16.6 | 10.2 | | |
| Total Yield [%] | 94.0 | 92.9 | | |

TABLE 5

Examples 17 to 20

| | Example | | | |
|---|---|---|---|---|
| | 17 | 18 | 19 | 20 |
| Hydrolysis conditions | | | | |
| NFGDA [mmol] | 200 | 200 | 200 | 200 |
| NaOH [mol equivalents] | 1.05 | 1.05 | 1.05 | 1.05 |
| Solvent | butan-1-ol | butan-1-ol | butan-1-ol | butan-1-ol |
| Amount of solvent [mol equivalents] | 9.7 | 7.0 | 5.0 | 5.0 |
| Concentration [% NFGDA] | 16.5 | 20.3 | 24.5 | 24.5 |
| Temperature [° C.] | 80 | 80 | 80 | 100 |
| Time [hour(s)] | 4.0 | 4.0 | 4.0 | 1.5 |
| Isolation method of GDA | Crystallisation & concentration of ML | Crystallisation & concentration of ML | Crystallisation & concentration of ML | second extraction of $H_2O$ Concentration |
| Isolation method of sodium formate Crystallisation | Phase separation | Phase separation | Phase separation | Phase separation |
| Temperature [° C.] | 20 | 1 | 20 | |
| Time [hour(s)] | 12 | 12 | 12 | |
| Yield Crystallisation [%] | 39.5 | 71.2 | 65.6 | |
| Yield Mother Liquor (ML) [%] | 47.1 | 18.0 | 26.4 | |
| Total Yield [%] | 86.6 | 89.2 | 92.0 | |

TABLE 6

Examples 21 to 24

| | Example | | | |
|---|---|---|---|---|
| | 21 | 22 | 23 | 24 |
| Hydrolysis conditions | | | | |
| NFGDA [mmol] | 200 | 200 | 200 | 200 |
| NaOH [mol equivalents] | 1.05 | 1.05 | 1.05 | 1.05 |

TABLE 6-continued

Examples 21 to 24

| | Example | | | |
|---|---|---|---|---|
| | 21 | 22 | 23 | 24 |
| Solvent | butan-1-ol | butan-1-ol | butan-1-ol | 2-methyl-propan-1-ol |
| Amount of solvent [mol equivalents] | 4.0 | 4.0 | 3.0 | 9.7 |
| Concentration [% NFGDA] | 27.4 | 27.4 | 30.9 | 16.5 |
| Temperature [° C.] | 80 | 100 | 80 | 80 |
| Time [hour(s)] | 4.0 | 4.0 | 4.0 | 4.0 |
| Isolation method of GDA | Crystallisation & concentration of ML | Crystallisation & concentration of ML | Crystallisation & concentration of ML | Crystallisation & concentration of ML |
| Isolation method of sodium formate | Phase separation | Phase separation | Phase separation | Phase separation |
| Crystallisation | | | | |
| Temperature [° C.] | 1 | 1 | 20 | 20 |
| Time [hour(s)] | 10' | 12 | 12 | 48 |
| Yield Crystallisation [%] | 73.3 | 71.3 | 69.1 | 47.7 |
| Yield Mother Liquor (ML) [%] | 20.6 | 19.1 | 18.4 | 42.7 |
| Total Yield [%] | 93.9 | 90.4 | 87.5 | 90.4 |

TABLE 7

Examples 25 to 28

| | Example | | | |
|---|---|---|---|---|
| | 25 | 26 | 27 | 28 |
| Hydrolysis conditions | | | | |
| NFGDA [mmol] | 200 | 200 | 200 | 200 |
| NaOH [mol equivalents] | 1.05 | 1.05 | 1.05 | 1.05 |
| Solvent | 2-methyl-propan-1-ol | 2-methyl-propan-1-ol | butan-2-ol | butan-2-ol |
| Amount of solvent [mol equivalents] | 7.5 | 7.3 | 15.0 | 10.0 |
| Concentration [% NFGDA] | 19.5 | 19.9 | 11.5 | 16.1 |
| Temperature [° C.] | 80 | 100 | 100 | 100 |
| Time [hou(s)] | 4.0 | 4.0 | 4.0 | 4.0 |
| Isolation method of GDA | Crystallisation & concentration of ML | second extraction of H$_2$O Concentration | second extraction of H$_2$O Concentration | second extraction of H$_2$O Concentration |
| Isolation method of sodium formate | Phase separation | Phase separation | Phase separation | Phase separation |
| Crystallisation | | | | |
| Temperature [° C.] | 20 | | | |
| Time [hour(s)] | 12 | | | |
| Yield Crystallisation [%] | 49.9 | | | |
| Yield Mother Liquor (ML)[%] | 38.8 | | | |
| Total Yield [%] | 88.6 | | | |

TABLE 8

Examples 29 to 32

| | Example | | | |
|---|---|---|---|---|
| | 29 | 30 | 31 | 32 |
| Hydrolysis conditions | | | | |
| NFGDA [mmol] | 200 | 200 | 200 | 100 |
| NaOH [mol equivalents] | 1.05 | 1.05 | 1.05 | 1.05 |

TABLE 8-continued

Examples 29 to 32

| | Example | | | |
|---|---|---|---|---|
| | 29 | 30 | 31 | 32 |
| Solvent | butan-2-ol | butan-2-ol | butan-2-ol | tetrahydrofuran |
| Amount of solvent [mol equivalents] | 9.7 | 7.5 | 7.1 | 20.0 |
| Concentration [% NFGDA] | 16.5 | 19.5 | 20.1 | 9.7 |
| Temperature [° C.] | 80 | 80 | 100 | 63 |
| Time [hour(s)] | 4.0 | 4.0 | 4.0 | 4.0 |
| Isolation method of GDA | Crystallisation & concentration of ML | Crystallisation & concentration of ML | Crystallisation & concentration of ML | Crystallisation & concentration of ML |
| Isolation method of sodium formate | Phase separation | Phase separation | Phase separation | Phase separation |
| Crystallisation | | | | |
| Temperature [° C.] | 1 | 20 | 1 | 20 |
| Time [h] | 12 | 12 | 12 | 48 |
| Yield Crystallisation [%] | 67.6 | 65.3 | 70.4 | 67.9 |
| Yield Mother Liquor (ML) [%] | 22.7 | 27.5 | 21.4 | 13.5 |
| Total Yield [%] | 90.3 | 92.8 | 91.8 | 81.4 |

TABLE 9

Example 33 (according to the process of the present invention)

| | Example 33 |
|---|---|
| Hydrolysis conditions | |
| NFGDA [mmol] | 200 |
| NaOH [mol equivalents] | 1.05 |
| Solvent | 1,2-dimethoxy-ethan |
| Amount of solvent [mol equivalents] | 9.7 |
| Concentration [% NFGDA] | 14.2 |
| Temperature [° C.] | 80 |
| Time [hour(s)] | 4.0 |
| Isolation method of GDA | Crystallisation & concentration of ML |
| Isolation method of sodium formate | Phase separation |
| Crystallisation | |
| Temperature[° C.] | 20 |
| Time [hour(s)] | 12 |
| Yield Crystallisation [%] | 83.8 |
| Yield Mother Liquor (ML) [%] | 8.5 |
| Total Yield [%] | 92.3 |

The examples 1, 2, 9, 12, 14 and 16 are described in more detail in the following.

Example 1

Preparation of GDA in Methanol

Under an Ar atmosphere 9.36 g (53.5 mmol) of NFGDA were suspended in 16.6 g of methanol. The suspension was stirred at 400 rpm and heated to 340 K (internal temperature). 6.97 ml (56.2 mmol) of a 25.17 weight-% sodium hydroxide solution were added within 30 minutes (0.23 ml/min). The mixture was stirred at 349 K for 4 hours. The mixture was cooled to 0° C. with an ice bath overnight and filtered. The crystals were dried at 333K, 20 mbar overnight.

4.26 g of light yellowish crystals were obtained with a purity of 62.25% GDA, analyzed by HPLC (int. standard), 20 ppm of 2-chloroaniline, 36.8% sodium formate, analyzed by HPLC (ext. standard), 0.7% water, analyzed by Karl-Fischer titration, 40 ppm of methanol, analyzed by headspace GC. Isolated yield 35.9% based on NFGDA. The mother liquors were evaporated under reduced pressure (10 mbar, 323 K) and dried at 333 K, 20 mbar overnight. 7.58 g of yellowish residue contained 58.56% GDA, analyzed by HPLC (int. standard), 27.0% sodium formate, 80 ppm of 2-chloroaniline, analyzed by HPLC (ext. standard), 11.4% water, analyzed by Karl-Fischer titration, 1 ppm of methanol, analyzed by headspace GC. Yield 60.0% based on NFGDA. The chemical yield of the reaction was 95.9% based on NFGDA. 56.3% of sodium formate were isolated in the mother liquors residue and 43.1% were detected in the light yellowish crystals of the isolated GDA.

Example 2

Preparation of GDA in Ethanol

Under an Ar atmosphere 18.72 g (107 mmol) of NFGDA were suspended in 47.8 g of ethanol. The suspension was stirred at 350 rpm and heated to 353 K (internal temperature). 18.64 g (112.3 mmol) of a 24.1 weight-% sodium hydroxide solution were added within 20 minutes. The mixture was stirred at 353 K for 3 hours 40 minutes. The sodium formate precipitated during the reaction. The mixture was cooled to room temperature and filtered. The crystals of sodium formate were dried at 323 K, 20 mbar overnight. 4.86 g of white crystals were obtained with a purity of 94.04% of sodium formate, analyzed by HPLC (ext. standard), 0.88% GDA, analyzed by HPLC (int. standard). 62.8% of sodium formate based on NFGDA were isolated. The alcohol solution was evaporated under reduced pressure (10 mbar, 313 K).

19.03 g of yellowish crystals were obtained with a purity of 68.28% GDA, analyzed by HPLC (int. standard), 12.1% of sodium formate, 610 ppm of 2-chloroaniline, analyzed by HPLC (ext. standard), 13.5% water, analyzed by Karl-Fischer titration, 280 ppm of ethanol analyzed by headspace GC. Isolated yield 87.9% based on NFGDA. The chemical yield of the reaction was 88.2% based on NFGDA. 31.6% of sodium formate were detected in the light yellowish crystals of isolated GDA.

Example 9

Preparation of GDA in propan-2-ol (Isolation of GDA by Concentration of the Organic (Alcohol) Phase)

Under an Ar atmosphere 52.5 g (300 mmol) of NFGDA were suspended in 175 g of propan-2-ol. The suspension was stirred at 400 rpm and heated to 355 K (internal temperature). 38.95 ml (315 mmol) of a 25.35 weight-% sodium hydroxide solution were added within 30 minutes (1.3 ml/min). The mixture was stirred at 356 K for 5 hours. The liquid-liquid phase separation was carried out at 353 K. 10 ml of distilled water were added to the water phase in order to avoid crystallisation of sodium formate. The water phase was extracted at room temperature with 3×15 ml of propan-2-ol. 60.81 g of water phase were obtained containing 28.92% sodium formate, analyzed by HPLC (ext. standard). GDA and 2-chloroaniline were not detected, analyzed by HPLC (int./ext. standard). The combined organic phases were evaporated under reduced pressure (10 mbar, 323 K) and dried at 333 K, 20 mbar overnight. 1430 ppm of 2-chloroaniline were detected in the distilled propan-2-ol.

45.84 g of light yellowish crystals were obtained with a purity of 87.09% GDA, analyzed by HPLC (int. standard), 390 ppm of 2-chloroaniline, 4.5% of sodium formate, analyzed by HPLC (ext. standard), 8.3% water, analyzed by Karl-Fischer titration, 420 ppm of methanol, analyzed by headspace GC. Isolated yield 96.3% based on NFGDA. 86.2% of sodium formate were isolated in water phase and 10.1% were detected in the light yellowish crystals of the isolated GDA.

Example 12

Preparation of GDA in propan-2-ol (Isolation of GDA by Crystallisation from the Organic (Alcohol) Phase)

Under an Ar atmosphere 52.5 g (300 mmol) of NFGDA were suspended in 72.1 g of propan-2-ol. The suspension was stirred at 500 rpm and heated to 356 K (internal temperature). 39.1 ml (315 mmol) of a 25.17 weight-% sodium hydroxide solution were added within 30 minutes (1.3 ml/min). The mixture was stirred at 357 K for 3.5 hours. The liquid-liquid phase separation was carried out at 343 K. 10 ml of distilled water were added to the water phase in order to avoid crystallisation of sodium formate. The water phase was extracted at room temperature with 3×15 ml of propan-2-ol. 53.97 g of water phase were obtained containing 33.24% sodium formate, trace of 2-chloroaniline, analyzed by HPLC (ext. standard) and <0.1% GDA, analyzed by HPLC (int. standard). The combined organic phases were cooled to 0° C. with an ice bath overnight and filtered. The crystals were dried at 333 K, 20 mbar overnight.

33.20 g of white crystals were obtained with a purity of 95.60% GDA, analyzed by HPLC (int. standard), 130 ppm 2-chloroaniline, 4.4% of sodium formate, analyzed by HPLC (ext. standard), 1.0% water, analyzed by Karl-Fischer titration, trace of propan-2-ol, analyzed by headspace GC. Isolated yield 76.60% based on NFGDA. The mother liquors were evaporated under reduced pressure (10 mbar, 323 K) and dried at 333 K, 20 mbar overnight.

8.75 g of yellowish residue contained 79.60% GDA, analyzed by HPLC (int. standard), 6.1% of sodium formate, 1250 ppm of 2-chloroaniline, analyzed by HPLC (ext. standard), 8.1% water, analyzed by Karl-Fischer titration, 110 ppm of propan-2-ol, analyzed by headspace GC. Yield 16.8% based on NFGDA. The chemical yield of the reaction was 93.4% based on NFGDA. 87.8% of sodium formate were isolated in the water phase and 7.2% were detected in the white crystals of isolated GDA.

Example 14

Preparation of GDA in butan-1-ol (Isolation of GDA by Crystallisation from the Organic (Alcohol) Phase)

Under Ar atmosphere 35.0 g (200 mmol) NFGDA were suspended in 149 g of butan-1-ol. The suspension was stirred at 400 rpm and heated to 373 K (internal temperature). 26.1 ml (210 mmol) of a 25.17 weight-% sodium hydroxide solution were added within 30 minutes (0.87 ml/min). The mixture was stirred at 353 K for 1 hour. The liquid-liquid phase separation was carried out at 297 K. 10 ml of distilled water were added to the water phase in order to avoid crystallisation of sodium formate. The water phase was extracted at room temperature with 3×10 ml of butan-1-ol. 47.8 g of the water phase were obtained containing 24.6% sodium formate and 0.3% GDA analyzed by HPLC (int. standard). The combined organic phases were cooled to 0° C. with an ice bath overnight and filtered. The crystals were dried at 333 K, 20 mbar overnight.

24.2 g of white crystals were obtained with a purity of 94.50% GDA, analyzed by HPLC (int. standard), 95 ppm 2-chloroaniline, 3.9% of sodium formate, analyzed by HPLC (ext. standard), 1.0% water, analyzed by Karl-Fischer titration, 400 ppm of butan-1-ol, analyzed by headspace GC. Isolated yield 82.7% based on NFGDA. The mother liquors were evaporated under reduced pressure (15 mbar, 333 K) and dried at 333 K, 20 mbar overnight.

3.1 g of yellowish residue contained 91.60% GDA, analyzed by HPLC (int. standard), 0.8% of sodium formate, 650 ppm of 2-chloroaniline, analyzed by HPLC (ext. standard), 5.1% water, analyzed by Karl-Fischer titration, 500 ppm of butan-1-ol, analyzed by headspace GC. Yield 10.2% based on NFGDA. The chemical yield of the reaction was 92.9% based on NFGDA. 86.2% of sodium formate were isolated from the water phase and 6.9% were detected in the white crystals of isolated GDA.

Example 16

Preparation of GDA in butan-1-ol (Isolation of GDA by Concentration of the Organic (Alcohol) Phase)

Under an atmosphere of argon to 186.9 g (1000 mmol) of NFGDA were added 810 g of butan-1-ol. The suspension was stirred at 400 rpm and heated to 373 K (internal temperature). 129.8 ml (1050 mmol) of a 25.35 weight-% sodium hydroxide solution were added within 30 minutes (4.33 ml/min). The reaction solution was stirred at 373 K for 3.5 hours. At the end of the reaction the internal temperature was cooled to 313 K. The liquid-liquid phase separation was carried out at 313 K. 50 ml of distilled water were added to the water phase in order to avoid crystallisation of sodium formate. The water phase was extracted at room temperature with 3×50 ml of butan-1-ol. 186.6 g of the water phase were obtained containing 33.1% of sodium formate, analyzed by HPLC (ext. standard) and <0.1% of GDA analyzed by HPLC (int. standard). 2-Chloroaniline was not detected, analyzed by HPLC (ext. standard). The combined organic phases were evaporated under reduced pressure (20 mbar, 333 K) and dried at 333 K, 20 mbar overnight. 565 ppm of 2-chloro aniline were detected in the distilled butan-1-ol.

139.70 g of light yellowish crystals were obtained with a purity of 95.20% GDA, analyzed by HPLC (int. standard), 200 ppm of 2-chloroaniline, 3.6% of sodium formate, analyzed by HPLC (ext. standard), 0.9% of water, analyzed by Karl-Fischer titration, 650 ppm of butan-1-ol, analyzed by headspace GC. Isolated yield 96.2% based on NFGDA. 90.9% of sodium formate were isolated from the water phase and 7.4% were detected in the light yellowish crystals of isolated GDA.

The results concerning yield and purity of the examples 1 to 33 are summarized in the following Table 10.

TABLE 10

| Example | Solvent | Concentration of NFGDA [weight-%] | Temperature [° C.] | Reaction time [hour(s)] | Yield of product [%] | Purity of product = content of GDA in product [weight-%] | Content of 2-chloroaniline in product [ppm] | Not converted starting material [%] | Amount of separated sodium formate [% of formed amount] |
|---|---|---|---|---|---|---|---|---|---|
| 1 | MeOH | 26.5 | 76 | 4.5 | 95.9 | 62.2 | 20 | <0.1 | 56.3 |
| 2 | EtOH | 22.0 | 80 | 4.0 | 88.2 | 84.9* | 700* | n.f. | 62.8 |
| 3 | EtOH | 25.0 | 80 | 4.0 | 99.9 | 84.0* | 120* | 0.1 | 64.3 |
| 4 | PrOH | 18.8 | 80 | 5.0 | 93.9 | 92.9* | 1700* | 0.3 | 64.3 |
| 5 | PrOH | 30.0 | 94 | 4.5 | 91.7 | 90.8 | 20 | <0.1 | 86.4 |
| 6 | iPrOH | 16.4 | 82 | 4.0 | 95.3 | 87.9* | 250* | 0.9 | 72.5 |
| 7 | iPrOH | 18.8 | 80 | 4.5 | 93.4 | 93.8 | 2560 | 0.8 | 89.1 |
| 8 | iPrOH | 18.8 | 80 | 5.0 | 94.4 | 91.0 | 10 | 0.8 | 86.4 |
| 9 | iPrOH | 18.8 | 83 | 5.5 | 96.3 | 94.1* | 420* | 0.8 | 86.2 |
| 10 | iPrOH | 18.9 | 80 | 4.5 | 98.3 | 90.5 | 75 | 2.4 | 76.4 |
| 11 | iPrOH | 27.6 | 80 | 5.0 | 90.1 | 93.2 | 60 | <0.1 | 88.0 |
| 12 | iPrOH | 30.0 | 84 | 4.0 | 93.4 | 95.6 | 135 | <0.1 | 87.8 |
| 13 | iPrOH | 33.5 | 85 | 3.5 | 94.0 | 93.9 | <10 | <0.1 | 81.5 |
| 14 | BuOH | 16.1 | 100 | 1.5 | 93.4 | 94.5 | <5 | 0.2 | 86.2 |
| 15 | BuOH | 16.1 | 100 | 3.0 | 98.4 | 92.6 | 380 | 1.6 | 90.8 |
| 16 | BuOH | 16.1 | 100 | 4.0 | 96.2 | 95.2 | 200 | 0.2 | 90.9 |
| 17 | BuOH | 16.5 | 80 | 4.0 | 89.0 | 100.0 | 35 | 0.6 | 89.9 |
| 18 | BuOH | 20.3 | 80 | 4.0 | 93.0 | 87.6 | 10 | 0.1 | 88.8 |
| 19 | BuOH | 24.5 | 80 | 4.0 | 93.4 | 87.4 | 40 | n.f. | 90.3 |
| 20 | BuOH | 24.5 | 100 | 1.5 | 96.5 | 91.3 | 10 | 0.4 | 65.9 |
| 21 | BuOH | 27.4 | 80 | 4.0 | 96.2 | 97.4 | 30 | n.f. | 84.9 |
| 22 | BuOH | 27.4 | 100 | 4.0 | 93.2 | 87.8 | 60.0 | n.f. | 84.1 |
| 23 | BuOH | 30.9 | 80 | 4.0 | 89.8 | 94.1 | <5 | n.f. | 87.1 |
| 24 | 2-MePrOH | 16.5 | 80 | 4.0 | 90.9 | 97.2 | <5 | 0.7 | 90.3 |
| 25 | 2-MePrOH | 19.5 | 80 | 4.0 | 91.9 | 90.5 | 700 | 0.3 | 94.0 |
| 26 | 2-MePrOH | 19.9 | 100 | 4.0 | 96.8 | 90.7 | 170 | 1.4 | 89.5 |
| 27 | Bu2OH | 11.5 | 100 | 4.0 | 92.6 | 86.1 | 300 | 5.8 | 87.0 |
| 28 | Bu2OH | 16.1 | 100 | 4.0 | 98.2 | 95.0 | 130 | 2.1 | 93.7 |
| 29 | Bu2OH | 16.5 | 80 | 4.0 | 93.0 | 88.9 | 20 | 0.9 | 94.2 |
| 30 | Bu2OH | 19.5 | 80 | 4.0 | 93.6 | 90.3 | 20 | 0.5 | 91.5 |
| 31 | Bu2OH | 20.1 | 100 | 4.0 | 95.1 | 96.7 | n.f. | 1.3 | 89.8 |
| 32 | THF | 9.7 | 63 | 4.0 | 92.6 | 96.2* | <10* | 4.5 | 81.2 |
| 33 | DME | 14.2 | 80 | 4.0 | 94.2 | 100.0 | 55 | n.f. | 91.9 |

In the following

"MeOH" means methanol,

"EtOH" means ethanol,

"PrOH" means 1-propanol,

"iPrOH" means 2-propanol,

"BuOH" means 1-butanol,

"Bu2OH" means 2-butanol,

"2-MePrOH" means 2-methyl-propan-1-ol,

"DME" means 1,2-dimethoxyethane,

"THF" means tetra-hydrofuran,

"n.f." means not found,

*on dry basis.

The invention claimed is:

1. A process for the manufacture of Grewe-diamine with purity of at least 94% comprising:
hydrolyzing a compound of the formula II

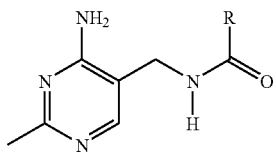

wherein R is hydrogen or straight- or branched-chain $C_{1-4}$ alkyl, with an aqueous alkali or alkaline-earth metal hydroxide solution characterized in that the hydrolysis is carried out in the presence of an organic solvent, and wherein the products of the hydrolysis are not further purified by sublimation.

2. The process as claimed in claim 1, wherein the organic solvent has a dielectric constant in the range of from 7 to 35.

3. The process as claimed in claim 1, wherein the organic solvent is an aliphatic alcohol, an ether or any mixture thereof.

4. The process as claimed in claim 1, wherein the organic solvent is essentially not soluble in water under the reaction conditions.

5. The process as claimed in claim 3, wherein the aliphatic alcohol is an aliphatic $C_{1-4}$-alcohol or any mixture thereof.

6. The process as claimed in claim 4, wherein the aliphatic alcohol is an ali-phatic $C_{3-4}$-alcohol.

7. The process as claimed in claim 3, wherein the ether is an ether in which Grewe-diamine is soluble.

8. The process as claimed in claim 7, wherein the ether is tetrahydrofuran or 1,2-dimethoxyethane.

9. The process according to claim 1 wherein R is hydrogen or methyl.

10. The process according to claim 1, wherein the hydrolysis is carried out at a temperature in the range of from 20 to 110° C.

11. The process as claimed in claim 6, wherein the alcohol is selected from the group consisting of propan-1-ol, propan-2-ol, butan-1-ol, butan-2-ol and 2-methyl-propan-2-ol.

12. The process as claimed in claim 11, wherein the alcohol is selected from the group consisting of propan-2-ol, butan-1-ol and butan-2-ol.

13. The process as claimed in claim 9, wherein the R is hydrogen.

14. A process for the manufacture of Grewe-diamine comprising the following step:
hydrolyzing a compound of the formula II

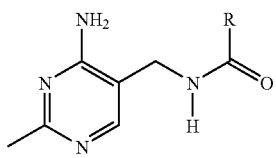

wherein R is hydrogen or straight- or branched-chain C1-4 alkyl, with an aqueous alkali or alkaline-earth metal hydroxide solution characterized in that the hydrolysis is carried out in the presence of an organic solvent.
wherein, the organic solvent is essentially not soluble in water under the reaction conditions.

15. A process for the manufacture of Grewe-diamine with purity of at least 94% comprising:
hydrolyzing a compound of the formula II

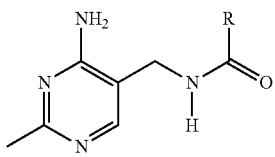

wherein R is hydrogen or straight- or branched-chain C1-4 alkyl, with an aqueous alkali or alkaline-earth metal hydroxide solution characterized in that the hydrolysis is carried out in the presence of an organic solvent.
wherein, the organic solvent is essentially not soluble in water under the reaction conditions.

16. The process as claimed in claim 15, wherein the organic solvent has a dielectric constant in the range of from 7 to 35.

17. The process as claimed in claim 15, wherein the organic solvent is an aliphatic alcohol, an ether or any mixture thereof.

18. The process as claimed in claim 15, wherein the organic solvent is essentially not soluble in water under the reaction conditions.

19. The process as claimed in claim 17, wherein the aliphatic alcohol is an aliphatic $C_{1-4}$-alcohol or any mixture thereof.

20. The process as claimed in claim 18, wherein the aliphatic alcohol is an ali-phatic $C_{3-4}$-alcohol.

21. The process as claimed in claim 17, wherein the ether is an ether in which Grewe-diamine is soluble.

22. The process as claimed in claim 21, wherein the ether is tetrahydrofuran or 1,2-dimethoxyethane.

23. The process according to claim 15 wherein R is hydrogen or methyl.

24. The process according to claim 15, wherein the hydrolysis is carried out at a temperature in the range of from 20 to 110° C.

25. The process as claimed in claim 20, wherein the alcohol is selected from the group consisting of propan-1-ol, propan-2-ol, butan-1-ol, butan-2-ol and 2-methyl-propan-2-ol.

26. The process as claimed in claim 25, wherein the alcohol is selected from the group consisting of propan-2-ol, butan-1-ol and butan-2-ol.

27. The process as claimed in claim 23, wherein the R is hydrogen.

* * * * *